United States Patent [19]

Stickl

[11] 4,053,582

[45] Oct. 11, 1977

[54] ATTENUATED FOWL POX VIRUS PREPARATION FOR THE TREATMENT OF INFECTIOUS DISEASES, METHOD FOR THE MANUFACTURE THEREOF, AND ITS USE

[76] Inventor: Helmut Anton Stickl, Starenweg 6,, 8033 Krailling B. Munich, Germany

[21] Appl. No.: 599,533

[22] Filed: July 28, 1975

[30] Foreign Application Priority Data

Aug. 1, 1974 Germany .............................. 2437166

[51] Int. Cl.$^2$ ........................ A61K 39/12; C12K 7/00
[52] U.S. Cl. ........................................ 424/89; 195/1.3
[58] Field of Search ............................ 195/1.3; 424/89

[56] References Cited

U.S. PATENT DOCUMENTS 3,429,965  2/1969  Gelenczei et al. ................... 195/1.3

OTHER PUBLICATIONS

Muntz et al. -Zentralblatt fur Veterinary Med. B, 21 (1974) pp. 442–454.

Primary Examiner—Sam Rosen
Attorney, Agent, or Firm—Gordon W. Hueschen

[57] ABSTRACT

Preparation for the treatment of interferon-sensitive infectious diseases for use in human and veterinary medicine, characterized by the fact that it contains as active principle a fowl pox virus which has been attenuated by 420 to 800 cell culture passages, optionally together with a pharmaceutical excipient or adjuvant, preferably containing a sufficient number of virus units so as to provide a total of $10^8$ to $10^{10}$ virus units per treatment involving 2 to 6 administrations thereof, method for the production thereof, method of producing pharmaceutical forms thereof, the pharmaceutical forms themselves, and a method of growing an effective fowl pox virus for use in the preparations of the invention.

14 Claims, No Drawings

ATTENUATED FOWL POX VIRUS PREPARATION FOR THE TREATMENT OF INFECTIOUS DISEASES, METHOD FOR THE MANUFACTURE THEREOF, AND ITS USE

The treatment of infection is being taxed today to a greater and greater extent by diseases, the pathogenic agents of which are present everywhere, persist in clinically healthy individuals, and in experiments do not make healthy individuals sick. These are essentially mixed infections, chronic and persistent infections, certain local infectious diseases, and infectious tumors.

Specific prophylaxis or treatment for these diseases is difficult and frequently impossible. One new very effective method of combatting them is afforded by interferonization.

By interferonization there is understood the medicinal production of rapid protection against infection by interferon. In this connection it is necessary to distinguish between:

1. passive interferonization (administration of exogenic interferon) and
2. active interferonization (medicinal induction of the active formation of endogenic interferon).

It is known that the production of interferon can be induced medicinally in humans and mammals. Chemical or socalled biological inducers are used for such induction. At present, the best known biological inducers of interferon are bacterial endotoxins as well as certain strains of virus, such as for instance the attenuated virus of infectious bovine rhinotracheitis and of infectious pustular vulvovaginitis. This is a matter of an animal herpes virus which is homologous for mammals and has a wide range of hosts. Despite its attenuation, it is still dangerous since latency and carrier properties are the rule and the animals treated therewith become chronic carriers. After administration it can multiply in the animal host.

Therefore, as viral interferon inducers, there have always been used strains of virus which could multiply in mammal cells of given species and whose non-dangerous nature was assured by natural non-virulence, by artificial attenuation, or by suitable inactivation.

It was not known heretofore that interferon can be induced in humans and mammals by animal viruses which cannot multiply in the organism of humans and mammals (heterologous viruses).

It has now been found that numerous infections in man and animals, for instance generalized Herpes, Herpes zoster, infections by influenza viruses, the Vaccinia virus, Papova viruses, and the virus of Condyloma acuminatum, can be successfully treated by a preparation which contains a strain of fowl pox virus which has been attenuated by numerous passages through a cell culture. This fowl pox virus is not pathogenic either for animals or for man.

The preparation in accordance with the invention furthermore enjoys possibilities for use in veterinary medicine to combat neonatal mortality caused by infections, infectious diseases at the start of the fattening of calves and pigs, infectious factor diseases and mixed infections, chronic diseases, viral tumors, local virus diseases of the urogenital tract, of the respiratory and digestive tracts, and of the skin.

The above effectivenesses are to be ascribed in particular to an active interferonization. In addition there can be noted a general increase in the resistance to infection which is due to other factors such as the increase in the phagocytosis rate.

Fowl pox virus is a block-shaped virus of 190 to 260 M$\mu$. It is of complex structure consisting of an outer sheath, two lateral bodies, a surface protein, and an inner body which contains double-stranded desoxyribonucleic acid. The large block-shaped viruses of the pox virus group belong to the differentiated viruses which are at the borderline from the bacteria with respect to size and structure. To be sure, there is still concerned a typical virus which multiplies exclusively in homologous living cells; particularly suitable nutrient media are fibroblast cells obtained from fowl embryos. In the present case, the fibroblasts of embryonated eggs of hens are obtained by trypsinization and seeded on the surface of the glass in a number of 500,000 to 800,000 cells/ml. The growth medium consists of 80% EARLE's solution, 10% beef embryo serum, and 10% lactalbumin. After incubation of the cells with this medium for 24 hours, a dense multi-layer cell mat has as a rule formed. The growth medium is removed and replaced by filtered bovine amnionic liquid. The virus is innoculated into the cell culture bottle and incubated for an additional 3 to 4 days. The virus is harvested between the 3rd and the 5th day depending on the development of the cytopathic effect. Multiplication of the virus on the chorioallantoic membrane (CAM) of embryonated eggs is also possible.

The following differences are present between the original fowl pox virus as it occurs in nature and the fowl pox virus which has been attenuated by multiple cell culture passages, i.e., robbed of its virulence:

No pathogenic properties for fowl or birds, particularly for day-old chicks (oral, intramuscular); no specific organotropy in case of massive innoculation in receptive organisms. Strong rapid multiplication in cell cultures, lytic plaques, strong production of interferon in the bird and mammal organism, increase of the phagocytosis rate and increase in the complement. This virus is no longer immunogenic for the natural host; however it still induces interferon. No differences can be noted on a rough morphological basis in an electron microscope between the attenuated Avipox virus and the original one. Serologically and immunobiologically the viruses which have been attenuated in cell cultures have not changed.

In the radial immunodiffusion method of Mancini, the attenuated viruses have 3 precipitation bands less than the original ones. There are concerned here one band from the lipoprotein fraction and probably 2 not yet precisely defined bands from the protein fraction of the virus. The pox viruses sediment out in salt medium even at 13,000 to 14,000 g within 20 minutes. In the sucrose gradient with 35% sucrose buffer solution, there is a concentration at the separation layer. This method is used for the purification of the viruses.

Upon oral administration of the attenuated fowl pox virus, a high degree of removal of foreign proteins is to be sure not necessary provided, merely that it is guaranteed that no pathogenic outside viruses are present in the preparation.

The attenuated fowl pox virus is relatively resistant to the environment; it is stable in water at a pH of 7.2 to 7.8. In freeze-dried condition it can be kept for a practically unlimited length of time. An additional improvement in its life can furthermore be obtained by addition of albumin peptone or dextran. Disinfection and inactivation of the virus is possible by lipophilic solvents as well as detergents (acetone, chloroform, alcohol, benzene; but not ether).

The starting point for the conversion into the new virus is the fowl pox virus. The new virus can be obtained in the following manner:

Preparation 1

A fowl pox virus is brought onto cell cultures of fowl fibroblast cells. The densely grown mat is infected by these viruses and destroyed within 3 to 5 days. When the cell mat has been more than 50% destroyed and the remaining cells show the cytopathogenic effect due to the virus, the medium is harvested with the remaining cells. Further digestion of the cells is effected by freezing and thawing and thereupon treating with ultrasonics. The harvesting of the infected chorioallantoic membranes (CAM) is effected at the end of 72 hours and 96 hours, i.e., after satisfactory formation of the primary foci and generalization over the entire membrane.

From the virus harvest the coarse cell components which remain after ultrasonic treatment are sedimented by lowspeed sedimentation at 120 – 600 g and discarded; the supernatent material is used for the obtaining of the virus. The obtaining of the virus can be effected by high-speed centrifuging (at 30,000 g) for 30 minutes in the cold, by precipitation, or by freeze-drying. In the latter case all salts and protein components are still in the cell medium.

After recovery of the sediment, the sediment which contains the Avipox virus is placed in (one tenth by volume of the starting solution) buffered sodium-chloride solution; peptone or 4% beef albumin is added for stabilization, followed by lyophilization. The dry powder, which contains, as solubilizer and preservative, in addition to the virus also peptone, dextran, or albumin, is now analyzed with respect to the virus content and used for the compressing of the tablets.

The attenuation by growth of the virus in multiple cell culture passages was brought about in the following manner:

Preparation 2

At 4 to 6 day intervals 1/20 to 1/40 of the virus containing medium was transferred from one flask to the next flask which was grown with a fowl fibroblast cell culture. After each third cell culture passage, proof of the identity of the virus was carried out serologically and biologically (Identity Test). Another identity test is effected on basis of the markers present (size of plaques, electron-optic examination of the block-shaped viruses, etc.). If the identity test is positive, further propagation of the virus is effected in the next flask which is grown with cells. After only 190 passages a clear decrease in virulence and pathogenity of the viruses can be observed upon infection of cortisone chicks or upon the innoculation of day-old chicks (i.v.). After the 420th passage this virus is not pathogenic either for man or for birds. The virus can be used after an additional 30 cell culture passages and clonization via three plaque-final dilution passages. Between the 420th and the 800th cell culture passage the virus is stable and has identical properties. In this region and beyond it can be used for the production of the preparation in accordance with the invention (Consistency Test).

Preparation 2a

Another method of growing viruses for the obtaining of constant attenuated strains results from the transfer to the embryonated egg: the air chamber is aspirated and the egg membrane (chorioallantoic membrane) is lowered on the side of the egg. At this place 0.2 ml of the virus-containing material is innoculated. After 4 days the egg membrane is recovered, washed in antibiotic-containing sodium chloride solution, and frozen in a deep freeze cabinet between −40° and −80° C. The virus remains stable in this egg membrane culture. In this way access to "fresh" material of earlier cell culture passages is possible at the time of production. For the production of the preparation in accordance with the invention, antibiotics are not used in any step of the production. For this there are only used eggs of leukose-free fowl which have been monitored with respect to their health.

The preparation of the invention can be administered locally, systemically, orally, nasally, intracutaneously and intramuscularly. The subcutaneous and intramuscular administration is less effective; however, here also there is an interferonization which can still be detected.

Stable attenuated strain-deposited culture

The active portion both of the solid preparation of the invention and of the liquid preparation is the attenuated fowl pox virus of the 432nd to 800th passage. The 429th cell culture passage was purified by triple clonization (432nd passage). It is the seed virus for the production and the starting virus for all further virus cell passages. It has been filed under the deposit designation "Mayr-Stickl-Avipox-Interferon-Inducer" with the State Innoculation Institute of Northrhine Westphalia, Department for Virus Growth and Testing, Dusseldorf 4, and can be used in this form for identification by comparison of the markers. This strain has been released for delivery to the public. The stability and identity of the virus in the further passages has been proven. Viruses of high cell-culture passages are as a rule unstable to the environment, but specifically this attenuated virus strain has substantially retained its resistance to the environment.

The manufacture of the preparations in accordance with the invention will be explained in further detail below on a basis of examples.

EXAMPLE 1

By decantation, the supernatent liquid of the cell culture which has been centrifuged off is separated from the sediment which contains the virus, the sediment is extracted and lyophilized with the addition of peptone and skimmed milk. The skimmed milk serves here simultaneously as pressing material for the production of tablets which furthermore can also be solidified by addition of synthetic polysaccharides, microcrystalline cellulose, lactose, silicates, talcum, yeast, or urea. The addition of urea imparts greater hardness to the tablets and permits better persorption of the virus. One condition for the stability of the virus is a pH prior to lyophilization of 7.2 – 7.8, preferably 7.4. Since skimmed milk has an acid pH, careful adjustment of the pH in advance is necessary.

Pathogenic yeast, Saccharomyces boulardii, has proven suitable as stabilizer. The adsorption of the Avipox virus on this yeast increases the effectiveness of the preparation and its stability. The tablets obtained in this manner do not contain any very finely divided silica or silicates, since the virus is to be liberated as completely as possible in the mucous membrane of the mouth.

One tablet has for instance the following composition by weight:

|   |   |   |
|---|---|---|
|   | 12 mg | virus with 2 × 10⁷ VU and peptone |
|   | 68 mg | Saccharomyces-polysaccharides |
|   | 8 mg | salts from the nutrient medium |
|   | 100 mg | talcum |
| abt. | 400 mg | powdered skimmed milk |
| abt. | 588 mg | = large flat tablets, relatively soft and hygroscopic. |

(VU = Viral Units = plaque-forming units per ml. of virus suspension)

EXAMPLE 2

For the production of a liquid preparation, for instance in the form of a spray for nasal use, the virus is placed in a quantity of 2 to 6 × $10^7$ VU/ml in Ringer's solution with 2% glycerin (pH 7.2) and stored in the cold. The liquid solution contains a color indicator, for instance phenol red, in order to check the pH. Ringer's solution is used in order to avoid the burning in the mucous membrane of the nose caused by osmotic gradient; the addition of glycerin serves to stabilize the preparation and to assure better adherence of the active substance.

The compressed tablets after lyophilization and drying are stored in an inert gas at +4° C. The virus contained in the Ringer-glycerin solution can also be stored at +4° C; before use this solution is again carefully mixed. Immediately before use it is filled into small plastic spray bottles. There is nothing to prevent a further addition of other therapeutic agents, such as for instance suitable essential oils or antibiotics. In industrial manufacture, additions of glycerin of 2 to 20% for preservation, as well as of a mixture of neomycine and bacitracin, as example of one possible antibiotic or other preservative and at the same time antibacterially acting substances, are used. In this way it is made possible at the same time to inhibit ordinary germs, i.e., germs which, in case of damage to the mucous membrane, or which after a virus-produced disease of man, settle in increased manner in the daily environment, acquire the capability of invasion, and thus in their turn again can lead to pathogenic phenomena (virus-bacteria synergism). Examples of this are Streptococci of the skin, Bacterium coli, the ubiquitous Staphylococci, Pseudomonas pyocyanea, and the Klebsiellae.

For use in human medicine the concentration per tablet should contain at least $10^5$ units capable of propagation in cell cultures. As a rule 2 to 5 × $10^7$ VU (plaque-forming units/ml virus suspension) per tablet are sufficient. The total dose of a treatment extending over two days is at least $10^8$ VU to a maximum $10^{10}$ VU. Maximum doses are readily possible. The dose depends on the indication. It is the highest in the case of Herpes genitalis and in the treatment of Condylomata acuminata and can be kept low in the treatment of Herpes simplex labialis. The number of tablets depends on these rules of dosage.

10–20 tablets of 0.4 g each in accordance with Example 1 are taken one to three times by the patient at intervals of 6 to 12 hours. In the case of Herpes zoster the dose should be doubled, as is true also in the case of Herpes genitalis. The preparation is atoxic, avirulent, and apathogenic up to a hundred times the dose. In Herpes zoster it may be necessary, in addition to increasing the dose, also to administer it several times. In this connection it should be borne in mind that interferon tolerance can occur in the case of induced interferon.

Without prejudice to the animal experiments carried out for the scientific investigations, the following practical fields of use result: newborn foals could be protected by the preparation effectively against equine influenza; newborn pigs, still sensitive to a number of virus infections of man and animal, can be effectively protected against virus-caused pigsty epidemic. They also show greater increases in weight and better development than the comparison groups. Natural conditions resulted when chicks received the medicine of the invention in their drinking water. Loss and growth rates were more favorable for the breeder. One particular advantage of the preparation of the invention for use in veterinary medicine is that, in contradistinction to the antibiotics frequently used for this purpose, it is completely degraded in the body of the animal.

In animal experimentation it was also possible to control Columbia SK infection. Even the mortality rate of mice after infection by Listeria-monocytogenes was decreased 50% by interferonization and parallel increase of phagocytosis reduced by 50%.

An examination of the interferon-inducing action of the new strain on dogs was carried out as follows:

| Group | No. of dogs | Treatment and manner of treatment |
|---|---|---|
| 1 | 3 | Intraperitoneal injection with 5 ml fowl pox suspension[x] |
| 2 | 3 | Nasal administration of 1 ml fowl pox suspension[x] for 3 consecutive days |
| 3 | 2 | Intraperitoneal injection with 5 ml physiological salt solution |

[x]The Avipox suspension contained $10^7$ $TCID_{50}$/ml (Tissue Culture Infective Dose which causes an infection in 50% of the cases)

Before and after the treatment a blood sample was taken of all the dogs in order to determine the interferon content of the serum. The interferon was not concentrated before the determination. The interferon content was determined by the end-point method in which canine herpes virus was used as virus and primary canine renal cell cultures as cell system.

The results obtained are set forth in the following table.

| No. of days after the treatment | Interferon level[x] in the serum | | |
|---|---|---|---|
| | Group 1 | Group 2 | Group 3 |
| −1 | — | — | — |
| 0 | — | — | — |
| 2 | 16 | 16 | — |
| 3 | 16 | 16 | — |
| 6 | 80 | 16 | — |
| 7 | 16 | 32 | — |
| 8 | 16 | 32 | — |
| 9 | 16 | 140 | — |
| 10 | 32 | 250 | — |

[x]Reciprocal of level per ml.

The above results show that the preparation of the invention upon intraperitoneal administration produces a rapid steep increase in the interferon content, while with nasal administration a more slowly increasing but substantially higher level can be noted.

The administration of the preparation in accordance with the invention and the results obtained in this connection will be described below on basis of Herpes eruptions since the success of the treatment is clearly evident here on the skin.

Case 1

Patient A, male, 25 years of age, Herpes genitalis with localization on the glans penis and on the body of the penis. Exacerbation of the phenomena about 1 week before the start of the treatment. On the average manifestation every 8 weeks, incomplete healing, permanent itching syndrome, afterpains after healing. Upon renewed exacerbation considerable local complaints and swelling of the glans. 20 tablets in accordance with Example 1 were given 3 times at intervals of 6 hours, on an empty stomach, in each case one half hour before meals. The tablets were chewed. The patient was free of complaints after only 4 hours. The skin eruptions started to dry up within 24 to 48 hours. Another treatment with the same dose on the third day after the start of the treatment, still another on the fifth day: complete healing of the symptoms, complete cure of the mucous membrane.

Case 2

Patient B, female, recurrent Herpes corneae, already treated several times by abrasion. Tearing of eye, considerable pain on the cornea.

Treatment was effected with twice 20 tablets in accordance with Example 1, the first being taken at noon and the second at 6 p.m. Only 2 hours after the second dose an abating of the complaints could be noted. Within 48 hours the eruptions were completely healed; freedom from complaints.

Case 3

Patient C, female, 30 years of age, recurrent Herpes of the upper lip, in each case considerable complaints at time of menstruation. Duration about 10-14 days.

Two times 20 tablets were administered in accordance with Example 1. Within 48 hours, drying up of the eruptions and freedom from complaint. After four days cured. The recurrence which took place four weeks or later was substantially weaker and was treated in the same manner. The patient has been free of recurrence and complaints now for four months.

Case 4

Patient D, of female sex, five year old child, Herpes zoster of the right cheek, affecting also the eye, partially generalized, with individual eruptions on the hands (extensor side). 1st day of treatment: 40 tablets in accordance with Example 1; check-up on the next day. Reduction of the swelling. The eye is somewhat freer, but occurrence of new Herpes eruptions. Another treatment with 40 tablets. On the fourth day a drying of the eruptions and only a moderate residual reddening of the lower stratum of the skin could be noted.

Case 5

47 year -old man, extensive continuous contact with a female patient suffering from influenza. First indications of influenza were hoarse voice, scratchiness in the throat. Took morning and evening 8 tablets each in accordance with Example 1. Well after four to six hours. No further indications of illness. Several environmental illnesses.

Case 6

13 year-old boy with virus-caused warts on his fingers and on the back of both hands. Took 2 × 8 tablets in accordance with Example 1 of 5 × $10^6$ VU each. After 2 days clear recession, within 13 days complete cure.

I claim:

1. Preparation useful for the treatment of interferon-sensitive infectious diseases for use in human and veterinary medicine, characterized by the fact that it contains as active principle an effective amount of fowl pox virus, which has been attenuated by 420 to 800 cell culture passages, together with a pharmaceutical excipient or adjuvant.

2. Preparation according to claim 1, characterized by the fact that it is present in an isotonic salt solution, and may contain a color indicator.

3. Preparation according to claim 2, wherein the isotonic salt solution is Ringer's solution.

4. Preparation according to claim 2, wherein the color indicator is phenol red.

5. Preparation according to claim 1, characterized by the fact that it contains a sufficient number of virus units so as to provide a total of $10^8$ to $10^{10}$ virus units per treatment, each treatment involving 2 to 6 doses.

6. A method for active interferonization of humans against infectious diseases characterized by administering an effective amount of a preparation in accordance with claim 1 orally, nasally, intracutaneously, or interamuscularly.

7. A method for active interferonization of mammals against infectious diseases characterized by administering an effective amount of a preparation in accordance with claim 1 orally, nasally, intracutaneously, or intramuscularly.

8. A method of producing a preparation useful for the endogenic treatment of interferon-sensitive infectious diseases for use in human and veterinary medicine, characterized by (1) applying an original fowl pox virus to a cell culture of embryonated fowl eggs, (2) attenuating it by about 420 to 800 cell culture passages, (3) harvesting the medium with the remaining cells, (4) digesting the cells, (5) separating the coarse cell components from the virus, and (6) recovering the virus from the virus-containing supernatant material by centrifuging, precipitation, or freezedrying.

9. A method according to claim 8, wherein the recovered virus is combined with a pharmaceutical excipient or adjuvant into the form of a pharmaceutical formulation which can be administered locally, orally, nasally, intracutaneously, or intramuscularly.

10. A method according to claim 8, wherein, the attenuation includes the step of clonizing the culture.

11. A method according to claim 8, characterized by the fact that the nutrient medium used comprises fowl embryo fibroblast cells.

12. The method according to claim 8, wherein the cell culture is fibroblast cells from embryonated hens' eggs.

13. The method according to claim 12, wherein the cell culture growth medium is 80% Earle's Solution, 10% beef embryo serum, and 10% lactalbumin.

14. The method according to claim 8, wherein the fowl pox virus is passaged 429 times serially followed by a triple clonization to produce a seed virus for production and a starting virus for further cell passages designated "Mayr-Stickl-Avipox-Interferon-Inducer".

* * * * *

UNITED STATES PATENT OFFICE
CERTIFICATE OF CORRECTION

Patent No. 4,053,582   Dated Oct. 11, 1977

Inventor(s) Stickl

It is certified that error appears in the above-identified patent and that said Letters Patent are hereby corrected as shown below:

Col. 4, line 60: "Saccharomyces" should read --Saccharomyces--

Signed and Sealed this

Second Day of May 1978

[SEAL]

Attest:

RUTH C. MASON
Attesting Officer

LUTRELLE F. PARKER
Acting Commissioner of Patents and Trademarks